(12) United States Patent
Yanaga (10) Patent No.: US 7,189,567 B2
(45) Date of Patent: Mar. 13, 2007

(54) METHOD OF CULTURING HUMAN CHONDROCYTES

(76) Inventor: Hiroko Yanaga, Ambient Kokura 912, 16-1, Kumamoto 3-chome, Kokurakita-ku, Kitakyushu-shi, Fukuoka, 802-0044 (JP)

( * ) Notice: Subject to any disclaimer, the term of this patent is extended or adjusted under 35 U.S.C. 154(b) by 293 days.

(21) Appl. No.: 10/344,135

(22) PCT Filed: Aug. 8, 2001

(86) PCT No.: PCT/JP01/06815

§ 371 (c)(1),
(2), (4) Date: Feb. 7, 2003

(87) PCT Pub. No.: WO02/12451

PCT Pub. Date: Feb. 14, 2002

(65) Prior Publication Data

US 2003/0180943 A1 Sep. 25, 2003

(30) Foreign Application Priority Data

Aug. 9, 2000 (JP) ............................. 2000-241206
Dec. 15, 2000 (JP) ............................. 2000-381915

(51) Int. Cl.
*C12N 5/00* (2006.01)
(52) U.S. Cl. ...................... 435/373; 435/354; 435/357; 435/366; 435/375
(58) Field of Classification Search ................. 435/373, 435/375, 357, 366, 354
See application file for complete search history.

(56) References Cited

U.S. PATENT DOCUMENTS

| 5,304,740 | A | * | 4/1994 | Bozell et al. | 174/110 PM |
| 5,690,926 | A | * | 11/1997 | Hogan | 424/93.1 |
| 6,093,393 | A | * | 7/2000 | Rosenthal et al. | 424/93.21 |
| 6,150,163 | A | * | 11/2000 | McPherson et al. | 435/384 |

FOREIGN PATENT DOCUMENTS

WO WO 98/44874 10/1998

OTHER PUBLICATIONS

Green, W., "Articular Cartilage Repair: Behavior of Rabbit Chondrocytes During Tissue Culture and Subsequent Allografting," *Clinical Orthopaedics and Related Research*, 124:237-250 (1977).
Ting, V., et al., In Vitro Prefabrication of Human Cartilage Shapes Using Fibrin Glue and Human Chondrocytes, *Annals of Plastic Surgery*, 40(4):413-421 (1998).
K.T. Paige et al., "Injectable Cartilage", Plastic and Reconstructive Surgery, vol. 96, No. 6, pp. 1390-1398, Nov. 1995.
B. Froger-Gaillard et al., "Production of Insulin-Like Growth Factors and Their Binding Proteins by Rabbit Articular Chondrocytes: Relationships With Cell Multiplication", Endocrinology, vol. 124, No. 5, pp. 2365-2372, 1989.

P. Cuevas et al., "Basic Fibroblast Growth Factor (FGF) Promotes Cartilage Repair In Vivo", Biochemical and Biophysical Research Communications, vol. 156, No. 2, pp. 611-618, Oct. 1988.
J.G. Rheinwald et al., "Serial Cultivation of Strains of Human Epidermal Keratinocytes: The Formation of Keratinizing Colonies From Single Cells", Cell, Vol. 6, pp. 331-344, Nov. 1975.
A. Rodriguez et al., "Characteristics of Cartilage Engineered From Human Pediatric Auricular Cartilage", Plastic and Reconstructive Surgery, vol. 103, No. 4, pp. 1111-1119, Apr. 1999.
A.L. Aulthouse et al., "Expression of the Human Chondrocyte Phenotype In Vitro", In Vitro Cellular & Developmental Biology, vol. 25, No. 7, pp. 659-668, Jul. 1989.
M. Brittberg et al., "Treatment of Deep Cartilage Defects in the Knee With Autologous Chondrocyte Transplantation", The New England Journal of Medicine, vol. 331, No. 14, pp. 890-895, Oct. 1994.
S. Wakitani et al., "Repair of Rabbit Articular Surfaces With Allograft Chondrocytes Embedded in Collagen Gel", The Journal of Bone and Joint Surgery, vol. 71-B, No. 1, pp. 74-80, Jan. 1989.
J.E. Aston et al., "Repair of Articular Surfaces by Allografts of Articular and Growth-Plate Cartilage", The Journal of Bone and Joint Surgery, vol. 68-B, No. 1, pp. 29-35, Jan. 1986.
G. Bentley et al., "Homotransplantation of Isolated Epiphyseal and Articular Cartilage Chondrocytes Into Joint Surfaces of Rabbits", Nature, vol. 230, pp. 385-388, Apr. 1971.
Z. Nevo et al., "Adhesion Characteristics of Chondrocytes Cultured Separately and in Co-Cultures With Synovial Fibroblasts", Cell Biology International, vol. 17, No. 3, pp. 255-273, 1993.
A. J. Nixon et al., "Temporal Matrix Synthesis and Histologic Features of a Chondrocyte-Laden Porous Collagen Cartilage Analogue", Am. J. Vet. Res., vol. 54, No. 2, pp. 349-356, Feb. 1993.
Partial Translation of "Chondrogenesis and Microenvironment: Roles of Somatomedin-Like Growth Factors and Extracellular Matrix", Seikagaku (Journal of the Japanese Biochemical Society), vol. 55, No. 9, pp. 1067-1091, 1983.
Translation of Summary "Fundamental Studies on Transplantation of Auricular Perichondrum—Effect of Combined Use of Porous Polyethylene With Collagen as Artificial Extracellular Matrix", Showaikaisi (Journal of the Medical Department of the Showa University), vol. 59, No. 4, pp. 438-444, 1999.

(Continued)

*Primary Examiner*—L Blaine Lankford
(74) *Attorney, Agent, or Firm*—Finnegan, Henderson, Farabow, Garrett & Dunner, L.L.P.

(57) ABSTRACT

This invention provides a method for rapidly culturing a large amount of human chondrocytes to give normal chondrocytes or a mass thereof. The culture method comprises co-culturing human chondrocytes together with perichondral cells in the chondrogenic stage, as feeder cells, which support the proliferation ability of the chondrocytes, to allow rapid culturing of the human chondrocytes in a large amount.

9 Claims, 10 Drawing Sheets

OTHER PUBLICATIONS

Van Der Mark et al., "Relationship Between Cell Shape and Type of Collagen Synthesised as Chondrocytes Lose Their Cartilage Phenotype in Culture," *Nature* 267:531-532 (1977).

Van Osch et al., "In Vitro Redifferentiation of Culture-Expanded Rabbit and Human Auricular Chondrocytes for Cartilage Reconstruction," *Plastic and Reconstructive Surgery* 107(2):433-440 (2001).

Tristan De Chalain et al., "Bioengineering of elastic cartilage with aggregated porcine and human auricular chondrocytes and hydrogels containing alginate, collagen, and κ-elastin," *J Biomed Mater Res*, 44:280-288 (1999).

Bodo Kurz et al., "Articular chondrocytes and synoviocytes in a co-culture system: influence on reactive oxygen species-induced cytotoxicity and lipid peroxidation," *Cell Tiss Res*, 296:555-563 (1999).

Ken Okazaki et al., "Expression of Insulin-Like Growth Factor I Messenger Ribonucleic Acid in Developing Osteophytes in Murine Experimental Osteoarthritis and in Rats Inoculated with Growth Hormone-Secreting Tumor," *Endocrinology*, 140:4821-4830 (1999).

Carsten Perka et al., "Matrix-mixed culture: New methodology for chondrocyte culture and preparation of cartilage transplants," *J Biomed Mater Res*, 49:305-311 (2000).

M. Schulze et al., "Adulte humane chondrozyten in Alginatkultur," *Der Orthopäde*, 29:100-105 (2000), and English translation.

Office Action issued by European Patent Office, for EP 01 956 815.3, issued Jul. 6, 2006.

* cited by examiner

*Fig. 1*

(A)     CS21 cells (feeder cells) + human chondrocytes (B)

3T3 cells + human chondrocytes

Fig. 2 culture medium alone • multilayer cultivation

(A) Human cultured chondrocytes + PGA (B) Human cultured chondrocytes + Calcium alginate

*Fig. 9*

PGA + human dermis     PGA alone

*Fig. 10*

←Bone formation

Fig. 11

(A) HE staining (B) alcian blue + PAS staining (C) alcian blue + PAS staining

M:DNA marker
1: Human cultured chondrocytes mass 3 months after transplantation
3:Feeder cells
5:Feeder cells + human cultured chondrocytes
2,4,6:Mouse cells
Human collagen II cDNA fragment

METHOD OF CULTURING HUMAN CHONDROCYTES

This application is a 371 of PCT/JP01/06815 filed Aug. 8, 2001.

TECHNICAL FIELD

This invention relates to a novel method of culturing normal human chondrocytes and to the normal human chondrocytes obtained by the method. This invention also relates to a cartilage therapy material using the normal human chondrocytes obtained by the method.

BACKGROUND ART

In a living body, chondrocytes exist integrated in the matrix of the living cartilage and can be isolated from the matrix by treating the tissues with an enzyme such as collagenase. One of the methods of therapy devised in the field of treating cartilage-related diseases has been transplanting of isolated chondrocytes, especially autotransplantation of chondrocytes. For this purpose, trials conducted in animal experiments have attempted transplanting of isolated chondrocytes into defective articular cartilage (Bently, et. al., Nature 230, 385–388 (1971); Green, Clin. Orthop. 124, 237–250 (1977); Aston et. al., J. Bone Joint Surg. 68-B, 29–35 (1986); Wakitani, et. al., J. Bone Joint Surg. 71-B, 74–80 (1989)).

Normal chondrocytes are required in large amounts for autotransplantation, but since only a small amount of cartilage can be extracted in the case of humans, it has been very difficult to obtain chondrocytes in a sufficient amount required for transplant. It has been attempted in the past to culture human chondrocytes of articular cartilage, auricular cartilage and costal cartilage. However, due to the minimal amount of human chondrocytes that can be used for culturing and the lack of an effective established method for culturing human chondrocytes, it has either been impossible to maintain the primary culture, or else when the primary culture has been successful, the time required has been very long, from six to eight weeks (Brittberg, et. al., New Engl. J. Med. 331, 889–895 (1994); Aulthouse, et. al. In vitro Cell. & Develop. Biol. 25, 659–668 (1989); Ting, et. al., 40, 413–421 (1998); Rodriguez, et. al., Plast. Reconstr. Surg. 103; 1111–1119 (1999)).

On the other hand, in cases of animals other than human (mouse, rabbit, chicken, cow, etc.) culturing of chondrocytes has been successful in some cases because large amounts of chondrocytes are available for primary culture and chondrocytes are easily extracted from fetuses or the young, which have extremely soft cartilage (Bently et. al. Nature 230, 385–388 (1971); Langer, Clin. Orthop. 124, 237–250 (1977); Aston et. al., J. Bone Joint Surg. 68-B, 29–35 (1986); Wakitani, et. al., J. Bone Joint Surg. 71-B, 74–80 (1989)).

DISCLOSURE OF THE INVENTION

This invention therefore aims to provide a method of rapidly culturing human chondrocytes to obtain a large amount of normal chondrocytes and a mass thereof. This invention also aims to provide cartilage therapy materials using the obtained normal human chondrocytes or a cell mass thereof.

The inventor of this invention, as a result of intensive research, discovered that perichondral cells in the chondrogenic stage support the proliferation ability of human chondrocytes. It was also discovered that co-cultivation of human chondrocytes together with such perichondral cells used as feeder cells can rapidly produce a large amount of human chondrocytes, especially in primary culture. It was further discovered that normal characteristics are maintained in the chondrocyte on mass obtained by multilayer seeding and further culturing of the thus cultured human chondrocytes.

This invention therefore provides a method of rapidly culturing a large amount of human chondrocytes by co-culturing between human chondrocytes and perichondral cells in the chondrogenic stage, which are used as feeder cells to support the proliferation of human chondrocytes. Furthermore, a chondrocyte mass in a gel state can be obtained by multi seeding and culturing of the thus obtained human chondrocytes one or more times. The number of times of multilayer seeding will depend on the size of cultured cartilage tissue required, but from 3 to 4 times is generally preferable.

It is preferable to use chondrogenic-stage perichondral cells from a mammalian fetus as feeder cells for the human chondrocyte culturing method of this invention, and it is more preferable to use first arch cartilage, Meckel's cartilage perichondral cells. Especially preferable are chondrogenic-stage perichondral cells from a 13-day-old murine fetus.

The mammalian fetus used for the invention can be a fetus of any mammal, for example, a rodent (mouse, rat, rabbit, etc.), dog, ape, cow, goat or sheep. It is preferable to use a mammal such as mouse, for which detailed biological research on the viviparous period has been conducted.

This invention also provides normal human chondrocytes obtained by the method of invention, and a cell mass thereof. The human chondrocytes obtained by the method of the invention are integrated into the cartilage matrix which contains chondrocalcin, type II collagen and the like. The cultured chondrocytes also bind to each other through the cartilage matrix to form a gel-like cell mass. For the purpose of this invention, "normal human chondrocytes" means chondrocytes that maintain the characteristics of the original cartilage.

This invention also provides cartilage therapy materials consisting of materials incorporating the above-mentioned human chondrocytes or their cell mass. Any artificial or natural material can be used as the material incorporating the human chondrocytes or cell mass so long as it protects the chondrocytes for transplant from the surroundings and prevents them from diffusing and being absorbed. Those which can serve as scaffolding for the chondrocytes to be transplanted are preferred. Examples of such materials are collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans and human dermis. A proteoglycan or glycosaminoglycan may be sulfated.

This invention also includes treatment methods for cartilage-related diseases, that employ the cartilage therapy materials.

This invention also relates to the use of perichondral cells in the chondrogenic stage, which support the proliferation ability of chondrocytes, as feeder cells in the above-mentioned treatment method.

Human Chondrocytes

The method of the invention can be applied to the cultivation of human chondrocytes of any cartilage tissue such as auricular cartilage, costal cartilage, articular cartilage, intervertebral cartilage, or tracheal cartilage. Chondrocytes of auricular cartilage, costal cartilage and articular cartilage are especially suitable. Any articular cartilage, from the mandibular joint, upper arm joint, elbow joint, shoulder joint, hand joint, hip joint, waist joint or leg joint, can be used.

The chondrocytes used in the cultivation method of the invention can be isolated from human cartilage tissue by conventional methods. Chondrocytes are usually isolated by chopping the sampled cartilage tissue with a chopping knife or the like, treating the chopped cartilage with trypsin or collagenase (e.g. type II collagenase) and filtering to isolate the chondrocytes. The preferred procedure is as follows.

(1) The sampled cartilage tissue is disinfected with an antibiotic (for example, penicillin, kanamycin) or an antifungal agent (for example, amphotericin B) and then minced with a scalpel or a chopping knife.

(2) The minced cartilage tissue is treated with EDTA, kept stationary overnight in a medium containing trypsin (preferably at 4° C.), transferred into a medium containing type II collagenase (and kept stationary for 1 to 6 hours, if necessary) and incubated for 1 to 6 hours at 37° C.

(3) The treated cartilage is transferred to a culture medium containing fetal bovine serum and agitated gently in the culture medium for several hours. The resulting culture medium is filtered with a filter (for example, a 100-micrometer filter) to isolate the chondrocytes.

By this method, $0.5-1.0\times10^6$ human chondrocytes can be obtained from $0.5$ cm$^2$ of human cartilage tissue. The cultivation method of this invention can also be combined with known growth factors, especially those which stimulate proliferation of cartilage, such as FGF (for example, bFGF), IGF (for example, IGF-I) and/or bone morphogenetic protein 9 (BMP9).

Feeder Cells

Feeder cells are cells that contribute to cell cultivation by supporting the proliferation ability and differentiation ability of a specific tissue or cell. For example, 3T3 cells derived from fibroblast cells are known as a feeder cells which support the proliferation ability of epidermal keratinocytes (Green et. al., Cell 6, p. 331–344 (1975)). However no feeder cells have been known for chondrocytes, and especially for human chondrocytes.

The feeder cells used for the cultivation method of this invention are cells which support the proliferation ability of human chondrocytes when they are co-cultured and which allow the proliferated chondrocytes to maintain the characteristics of the original cartilage tissue, or specifically, to maintain the characteristics of sampled cartilage tissues.

Such feeder cells can be obtained by screening cells using the above-mentioned criteria, i.e. supporting of the proliferation ability of human chondrocytes, and maintenance of characteristics. In a concrete screening procedure, sample cells are co-cultured with human chondrocytes, it is examined whether the chondrocytes have proliferated and whether the extracellular matrix of the proliferated cells is the same as the original cartilage matrix. Cells to be screened can be those isolated from a living body (including a fetus or embryo) or a tissue thereof, or a cloned cell. Chondrogenic-stage perichondral cells from an animal, especially a mammal, will be referred to as the exemplary feeder cells of the invention.

It is preferable to use chondrogenic-stage perichondral cells from a mammal for which detailed biological research on the viviparous period has been conducted, e.g. a rodent (mouse, rat, rabbit), and especially chondrogenic-stage perichondral cells from a mouse. A preferred chondrogenic stage is the period of differentiation and formation of first arch cartilage-Meckel cartilage. For a mouse, this corresponds to a 13-day-old fetus. It is also possible for this invention to use first arch cartilage-Meckel perichondral cells of a vertebrate other than a mammal, for example, the embryo of a bird (chicken, etc.) as the feeder cells.

Although the feeder cells can be used for seeding without any treatment after they are isolated from the fetus or embryo, it is preferable to culture them in a suitable culture medium for about 10 to 14 days before use. The feeder cells can be subcultured (up to a $5^{th}$, and preferably $1^{st}-3^{rd}$ subculture), and preserved in a frozen state, preferably at a temperature and under conditions where the cell organelles are not destroyed. An example of such preservation is storage in DME medium containing a cryo-protectant such as 10% FBS, 10% glycerin, at $-130°$ C. or below. When the feeder cells are subcultured, it is suitable to change the medium about 3 times a week. The cryopreserved cells are thawed for use as the feeder cells.

Even though the feeder cells are used in the primary culture together with the chondrocytes, in some cases the proliferation of chondrocytes may be weak, in which case co-culturing may only be possible up to the $1^{st}$ subculture. It is therefore most effective and preferable to use the feeder cells at the time of primary culture. Before the co-culturing with chondrocytes, it is possible to eliminate the proliferation ability of the feeder cells by radiation (e.g. gamma rays, cobalt radiation) or chemical treatment. The chemical treatment can be performed with an anti-cancer agent such as mitomycin C or actinomycin D, or an antibiotic such as ampicillin.

Method of Culturing Human Chondrocytes

Conventional culture media suitable for cultivation of chondrocytes can be used for co-culturing the human chondrocytes and feeder cells (mainly in primary culture). In addition to hydrocortisone (HC) and fetal bovine serum (FBS) into the media, a proliferation factor such as human bFGF or human IGF-I is added (Cuevas et. al., Biochem. Biophys. Res. Commun. 156, 611–618 (1988); Froger-Gaillard et al., Endocrinology, 124, 2365–2372). An example of such a medium is a mixed medium of F-12 and DME (H) in a ratio of 1:1, with addition of FBS (preferably about 10%), human bFGF (preferably about 10 ng/ml), HC (preferably about 40 ng/ml) and human IGF-I (preferably about 5 ng/ml).

1) Primary Culture

The feeder cells pre-processed by radiation are seeded in a flask (in the case of a flask having a 75 cm$^2$ base area, a concentration of $1.0\times10^6$ cells is preferable), and the chondrocytes are seeded (preferably $0.5-1.0\times10^6$ cells) and then cultured at conditions suitable for the cultivation of the chondrocytes (e.g. 37° C., 10% $CO_2$). The cultivation is continued until the proliferated cells form a confluent monolayer (usually for 10–14 days).

2) Subculture

The subculture can be performed with the same culture medium as the primary culture (usually seven days for one subculture). When the cells obtained by primary culture are subcultured, in the case of auricular cartilage, the number of cells increases by 30 to 746 times from P0 (primary culture) →P6. In the case of costal cartilage, the number of cells increases by 65 to 161 times from P0→P4. When more chondrocytes are desired, the number of subcultures can be increased.

3) Multilayer Culturing

A gel-like chondrocyte mass can be obtained by multilayer seeding and culturing of chondrocytes obtained by one or more seedings, and preferably 3 to 4 seedings. In the obtained chondrocyte mass, the human chondrocytes are surrounded and connected by a cartilage matrix containing chondrocalcin and type II collagen to form a gel-like cell mass.

As mentioned above, the chondrocytes obtained by the cultivation method of this invention maintain the characteristics of the original cartilage tissue, i.e. the cartilage tissue used for the primary culture. Maintenance of characteristics of the original cartilage tissue can be confirmed by the morphology of the cultivated cells and the composition of extracellular matrix (for example, chondrocalcin, type II collagen, as well as hyaluronic acid, chondroitin, chondroitin sulfate and keratosulfate).

Cartilage Therapy Material

The human chondrocytes or the cell mass obtained by the invention is integrated into a biomaterial and used for transplant as a cartilage therapy material. Examples of biomaterials into which human chondrocytes or their cell mass may be integrated include: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans and human dermis, which may be used independently or in combination. Proteoglycans and glycosaminoglycans maybe sulfated. Those biomaterials separate the chondrocytes from the surroundings and prevent the chondrocytes for transplant from diffusing or being absorbed, and preferably can serve as a scaffold for the transplanted chondrocytes. The biomaterials can be in any form, for example, membrane such as sheet, porous bodies such as sponges, meshes such as knits, textiles, non-woven fabrics, cotton and the like. It is preferable to use a porous material because this will allow the chondrocytes to more easily adhere to the biomaterial and permeate inside to promote the formation of cartilage tissue.

When collagen is used as a biomaterial, it can be cross-linked. With increased strength by the cross-linking, the cartilage therapy material composed of the collagen can be stably fixed to the body by a staple or the like and can support the chondrocytes or cell mass with the necessary strength until the new cartilage tissue forms.

Moreover, the collagen can be solubilized to form a collagen solution for admixture with the chondrocytes or cell mass, and the mixture gelled, if necessary, for use as a cartilage therapy material. Conventional collagen solutions can be used and it is preferable to use an enzyme-solubilized collagen solution because this removes immunogenic telopeptides. It is also possible to form a cartilage therapy material by integrating or overlaying a mixture of collagen solution and chondrocytes into or onto a sponge, non-woven fabric or the-like.

When the materials into which the chondrocytes are integrated are properly selected, combined and shaped into a supporting body, the cartilage therapy material can not only form cartilage tissue but can also induce cartilaginous ossification. Human dermis is an example of such a material which induces cartilaginous ossification. Ossification can also be promoted by a growth factor which promotes bone formation, such as bone morphogenetic protein (BMP).

The invention will now be illustrated in detail by Examples. However, the invention is not restricted to these Examples.

BEST MODE FOR CARRYING OUT THE INVENTION

EXAMPLES

Example 1

Chondrocyte Cultivation

Culture-medium composition: To a mixed medium of F-12 and DME (H) in a ratio of 1:1 there were added 10% FBS, 10 ng/ml human bFGF (Kaken Pharmaceutical Research Institute), 40 ng/ml HC and 5 ng/ml human IGF-I (Gibco).

Chondrocytes: Chondrocytes were isolated from rear auricular cartilage (about 1×1 cm) and from precordial costal cartilage (about 1×1 cm) respectively.

Feeder cells: Cells surrounding first arch cartilage-Meckel cartilage of a 13-day-old mouse fetus were collected and cultivated to produce feeder cells, designated as CS21 cells.

(a) Isolation of Chondrocytes

A piece of cartilage was disinfected with Penicillin G (100 u/ml) and kanamycin (0.1 mg/ml) and processed with 0.02% EDTA for 15 minutes. The piece of cartilage was then chopped with a scalpel and chopping knife, kept stationary overnight at 4° C. in a medium containing 0.25% trypsin, and then incubated at 37° C. for 1–6 hours in DME medium containing 0.3% type II collagenase. It was then transferred into DME medium containing 10% FCS, gently agitated with a stirrer for 2 hours and filtered with a 100-micrometer filter to separate the chondrocytes.

(b) Feeder Cells i) Isolation of Feeder Cells

Cells surrounding first arch cartilage (Meckel cartilage) of a 13-day-old (chondrogenic stage) live Balb mouse fetus were collected using microsurgery technology. The obtained cell mass was transferred to a calcium-free culture medium containing 0.125% trypsin, left stationary in a refrigerator at 4° C. for 4 hours, agitated gently by a stirrer for 10 minutes and filtered to isolate single cells.

ii) Culture Conditions

The feeder cells were cultured in DME medium containing 5–10% FBS (fetal bovine serum). In primary culture, they became confluent in 3–4 days and in the first subculture they became confluent in 3–5 days. From the second subculture, the cells were subcultured every week and the $1^{st}$ to $3^{rd}$ subcultures were cryopreserved. The obtained cells (CS21 cells) were used as feeder cells.

(c) Primary Culture

Figure 1:
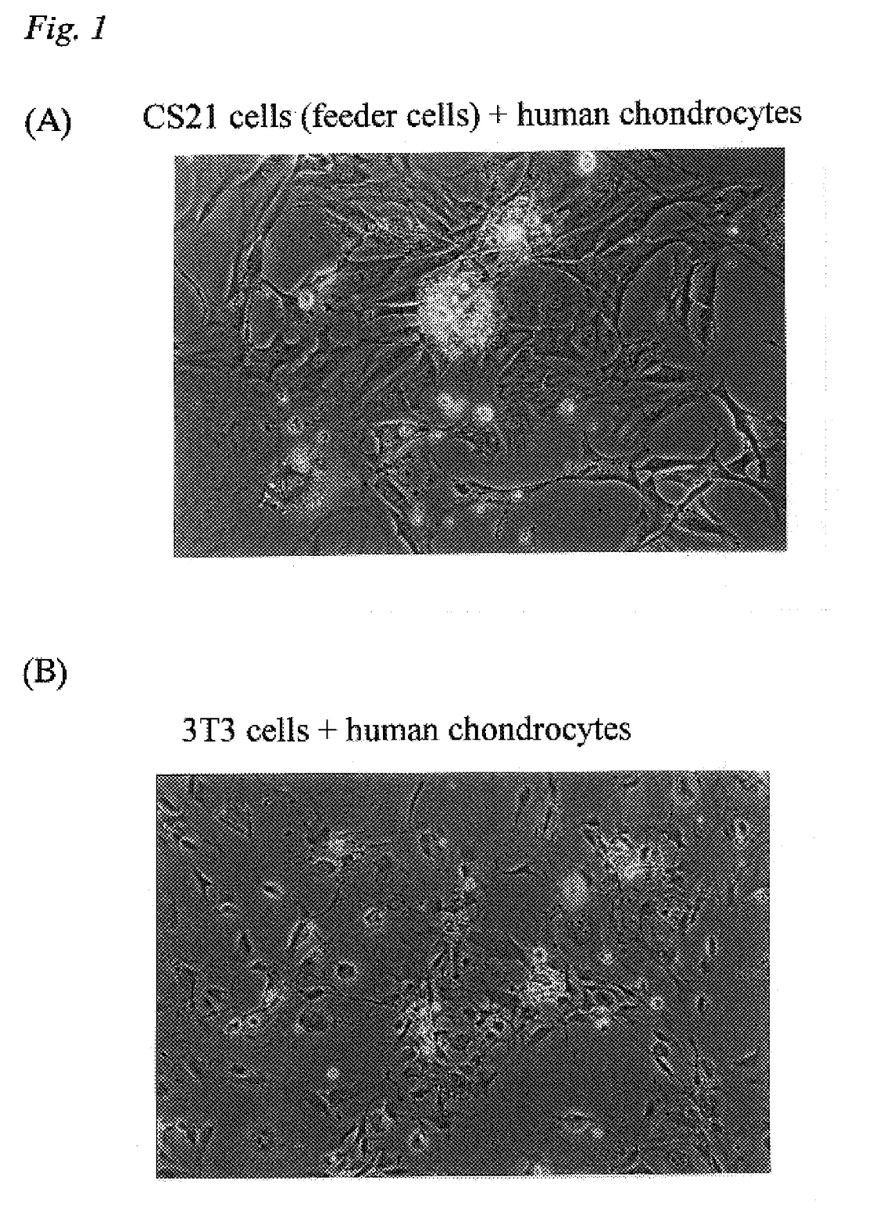
FIG. 1 is a set of photographs showing the results of the primary cultures of human chondrocytes together with (A) feeder cells (CS21 cells) of the invention and (B) 3T3 cells.

CS21 cells treated with 60 Gy of radiation (cobalt) on the previous day were seeded on a flask having a base area of 75 $cm^2$ at a density of $1.0 \times 10^6$ cells/$cm^2$. On the same flask, the isolated human chondrocytes were also seeded at a density of $0.5–1 \times 10^6$ cells/$cm^2$, and cultured at 37° C. under 10% $CO_2$. As a control, 3T3 cells were used as feeder cells under the same conditions. In the primary culture, the culture medium was exchanged two times a week. As a result, the chondrocytes co-cultured with CS21 cells became confluent in monolayer upon culturing for 10–14 days, whereas little growth was observed when 3T3 was used (FIG. 1). The obtained cells were used for the following subculture.

(d) Subculture of Chondrocytes

Subculture was carried out under the same conditions as the primary culture except that feeder cells were not used and the period of one subculture was 7 days. The human chondrocytes obtained by the primary culture were seeded on a flask at a density of $1.0 \times 10^6$ cells/175 $cm^2$ of the base area, subcultured every 7 days and cryopreserved after each subculture, and the increased number of chondrocytes was counted.

In the case of auricular cartilage (n=20), the cultivation was carried out by primary culture of auricular cartilage cells (n=20) P0→P1 (n=20) P1→P2 (n=13) P2→P3 (n=12) P3→P4 (n=9) P4→P5 (n=6) P5→P6 (n=3), and cells obtained at each subculture were cryopreserved. The cell count increase was about 30-to 746-fold.

In the case of the costal cartilage (n=12), the cultivation was carried out by the primary culture of costal cartilage cells (n=12) P0→P1 (n=12) P1→P2 (n=6) P2→P3 (n=4) P3→P4 (n=2), and the cells were cryopreserved in a similar manner. The cell count increase was about 65-to 161-fold.

When the concentrations of chondrocalcin, which is a component of cartilage matrix, in the culture media were measured by enzyme immunoassay (EIA) using anti-chondrocalcin antibody, chondrocalcin was detected at a concentration higher than 100 ng/ml both with the auricular cartilage and costal cartilage which were subcultured for 7 days. On the other hand, almost no cell proliferation was observed in the case of each chondrocytes cultured with no feeder cells or 3T in primary culture. The results of the cell cultures are shown in the following table 1.

TABLE 1

|  |  | Cartilage tissue | | | |
|---|---|---|---|---|---|
|  |  | Auricular cartilage | | Costal cartilage | |
|  |  | Feeder cell | | | |
|  |  | CS21 cells | Not used | CS21 cells | Not used |
| Cell proliferation | Primary culture | ++ | – | ++ | – |
|  | Subculture | +++ | NT* | +++ | NT* |

*not examined (primary culture failed, subcultivation impossible)

The results show that primary culture by the method of the invention can be achieved in 2 weeks, the cell proliferation rate is high, and a large amount of normal cells are rapidly cultured, while conventional culture-system without feeder cells cannot be maintained because establishing primary culture is difficult, and even if successful, it takes 6–8 weeks for primary cultivation. Furthermore, the fact that a large amount of chondrocalcin of cartilage matrix was present in the culture media suggests that the increased cells are chondrocytes.

(e) Multilayer Culturing

Figure 2:
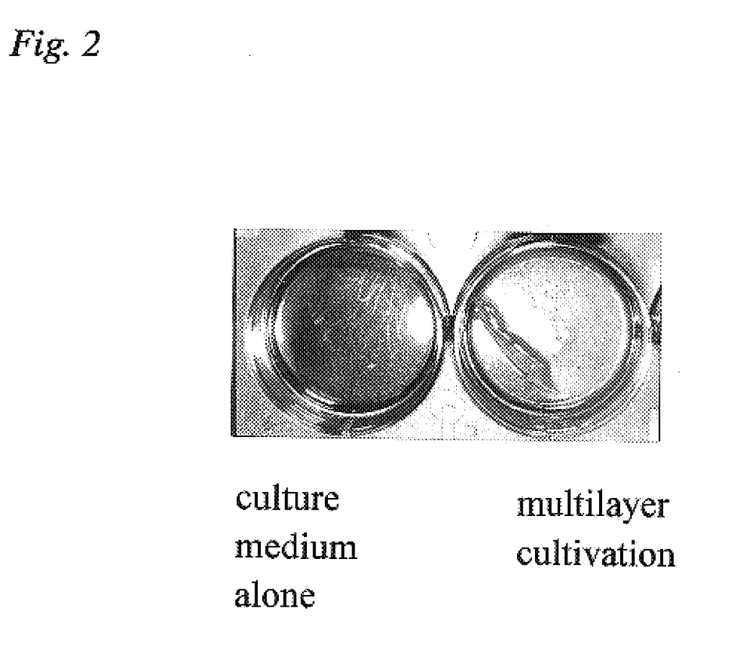
FIG. 2 is a photograph showing culture medium alone (left) and the result of multilayer cultivation (right).
Figure 3:
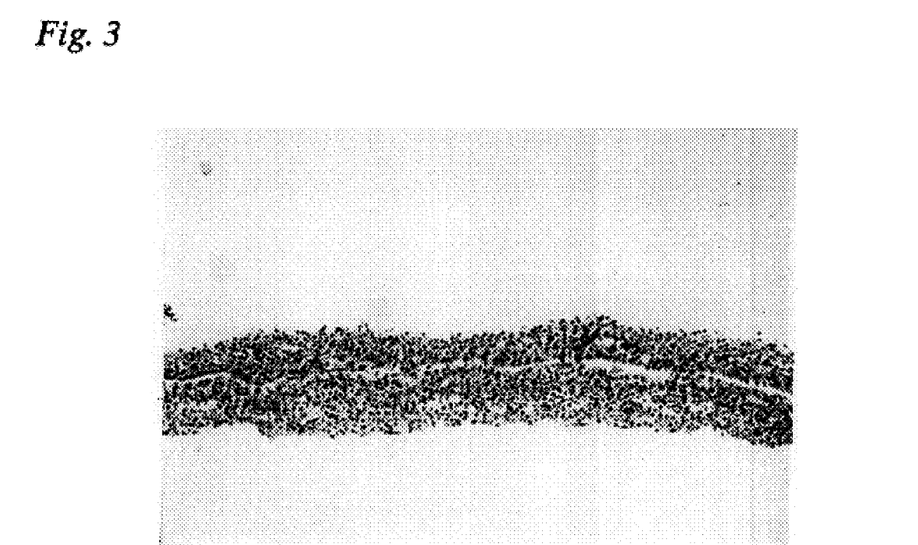
FIG. 3 is a microphotograph showing HE (hematoxylin-eosine) staining of a gel-like cell mass obtained by multilayer cultivation.
Figure 4:
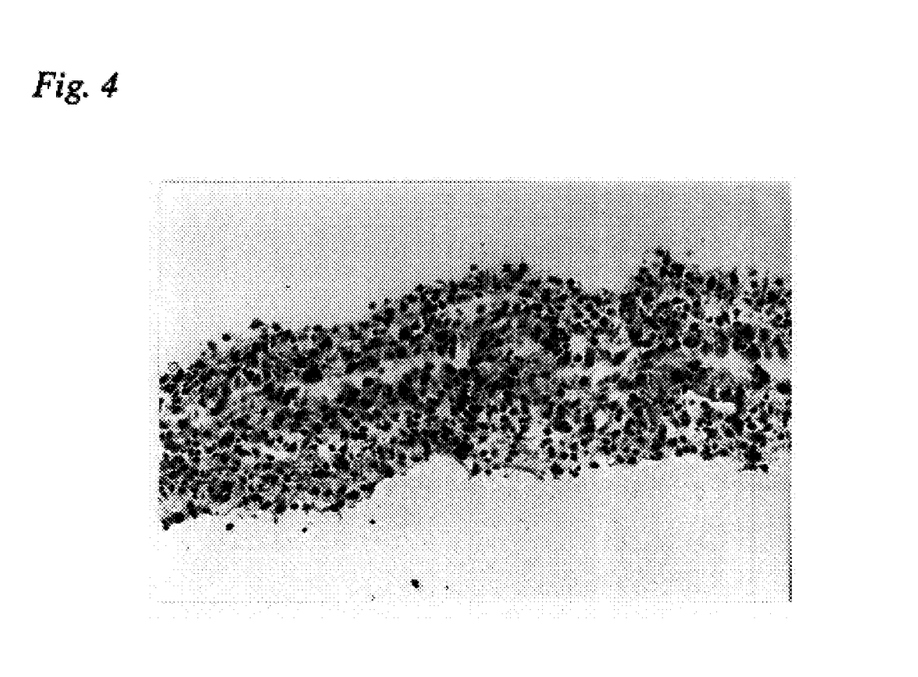
FIG. 4 is a microphotograph showing immunological staining using anti-type II collagen of a gel-like cell mass obtained by multilayer cultivation.

The chondrocytes obtained by the subculture were seeded by overlaying 3 times at a density of $1 \times 10^6$ cells/cm$^2$ and cultured by multilayer culturing. A sheet-like gel mass was formed after two weeks of culturing (FIG. 2). When the gel-like chondrocyte mass was stained by HE (hematoxylin-eosine) staining, the cells were seen to be multilayered and joined together through the matrix (FIG. 3). Moreover, when immunological staining was performed for type II collagen, which is a molecular marker of cartilage tissue, the extracellular matrix exhibited staining indicating that the extracellular matrix was a cartilage-specific matrix (FIG. 4).

Example 2

Transplanting of Chondrocytes
(a) In order to examine whether cartilage is formed without the influence of chondrocyte-integrating material (support) the obtained human chondrocyte mass was meshed in glass fiber (filter) and transplanted under the dorsal skin of nude mice (BALB/C Sic/nu, 10-week old, 25 g) (n=10). Formation of cartilage tissue was confirmed in 3/10 mice. Since large tissue did not form, it was conjectured that the chondrocytes were not stably held by the glass fiber and diffused into the surrounding tissues. Moreover, when the chondrocyte mass alone was transplanted, the chondrocytes were found diffused under the skin. It was thus shown that the chondrocyte mass for transplant must be protected from the surroundings.

Figure 5:
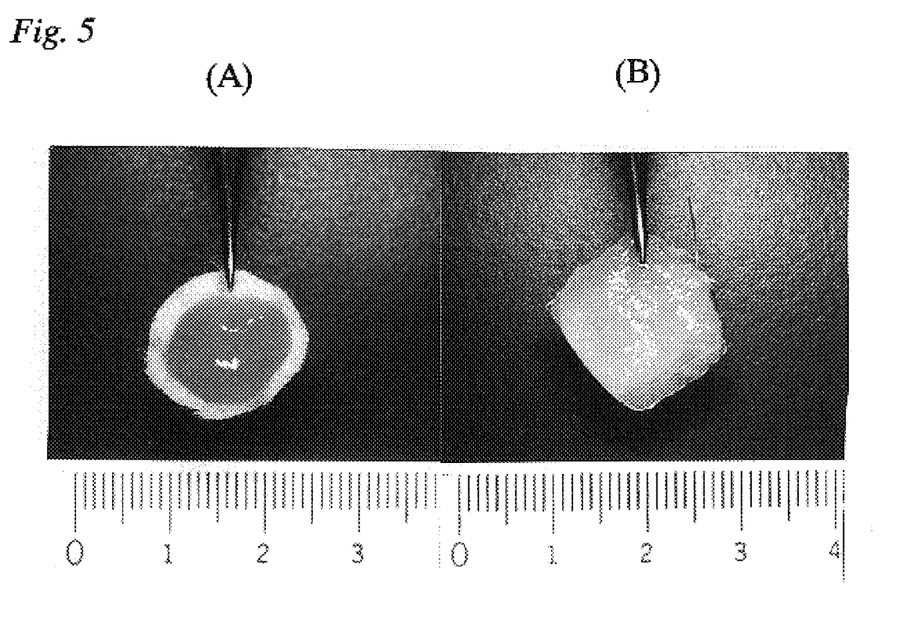
FIG. 5 is a set of photographs of (A) a material consisting of PGA as a support on which a human chondrocyte mass was overlaid and (B) a material consisting of PGA in which a chondrocyte mass was held.
Figure 6:
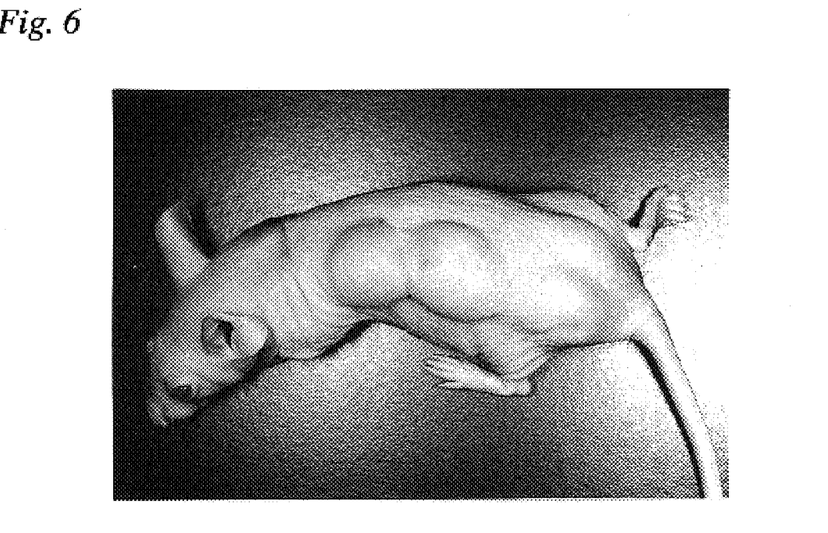
FIG. 6 is a photograph of a mouse three months after a chondrocyte mass was transplanted.
Figure 7:
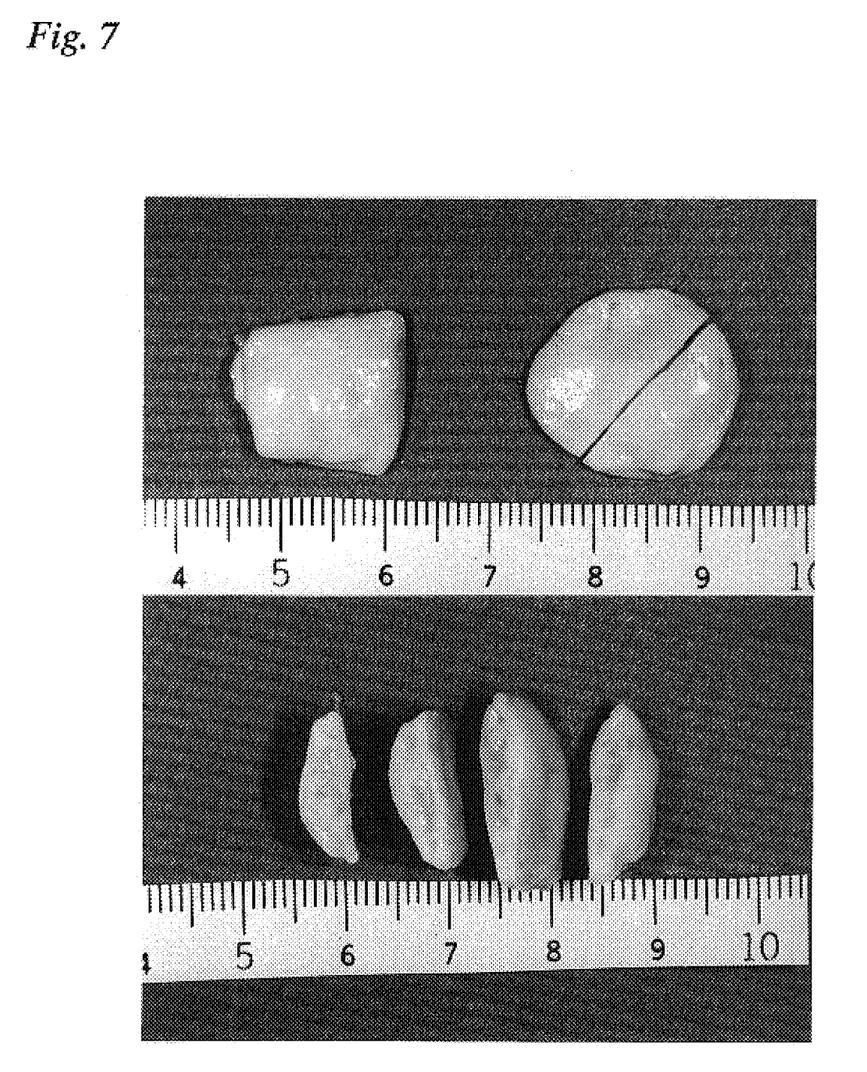
FIG. 7 is a set of photographs showing specimens extracted from the mice three months after transplant of the chondrocyte masses.

(b) The human chondrocytes were held in PGA (n=10) as a support, in such a manner that the chondrocytes were incorporated in the support, and transplanted into nude mice in the same manner. As a result, formation of cartilage tissue was observed in 100 percent of the samples (10/10). FIG. 5 shows the chondrocyte masses used for transplant, FIG. 6 shows a mouse three months after the transplant and FIG. 7 shows the specimens of the transplanted tissue.

Figure 8:
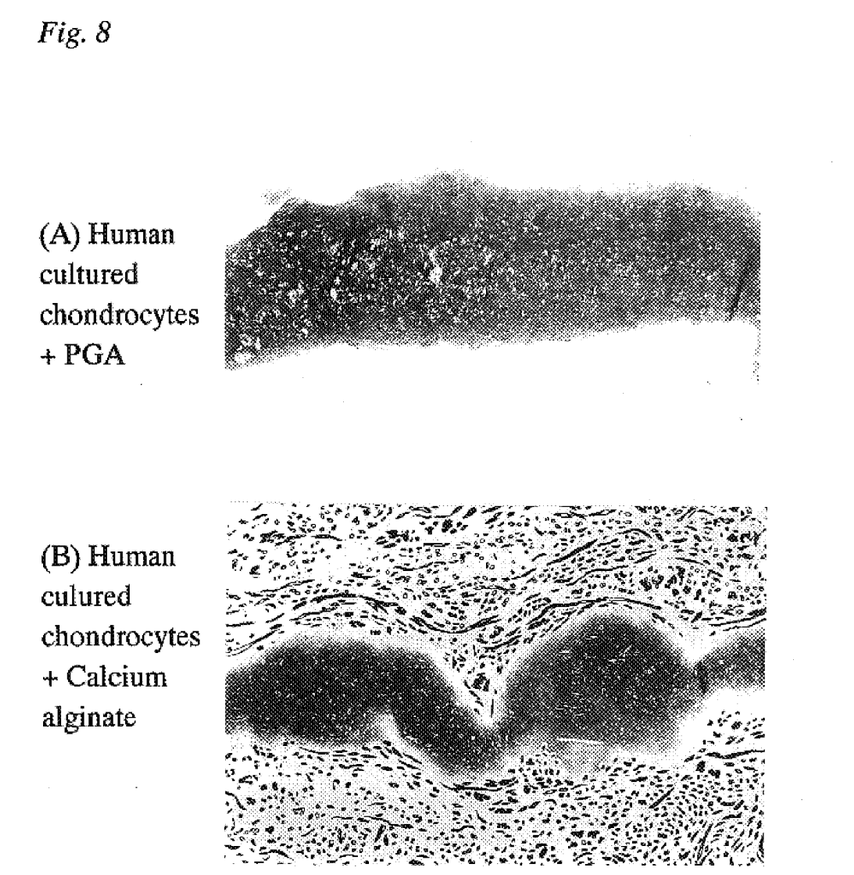
FIG. 8 is a set of microphotographs of extracted specimens stained with Toluidine Blue, wherein the supports were PGA (A) and calcium alginate (B).

Moreover, when calcium alginate (n=5) was used as a support, formation of cartilage tissue was also observed in 100 percent of the samples (5/5). The specimens using PGA and calcium alginate as support were then made into preparations for microscopy and stained with Toluidine Blue. As a result, the Toluidine Blue metachromacia specific to cartilage tissue was observed (FIG. 8). Since larger cartilage tissue was formed with PGA, it is conjectured that PGA is more suitable as a support.

Figure 9:
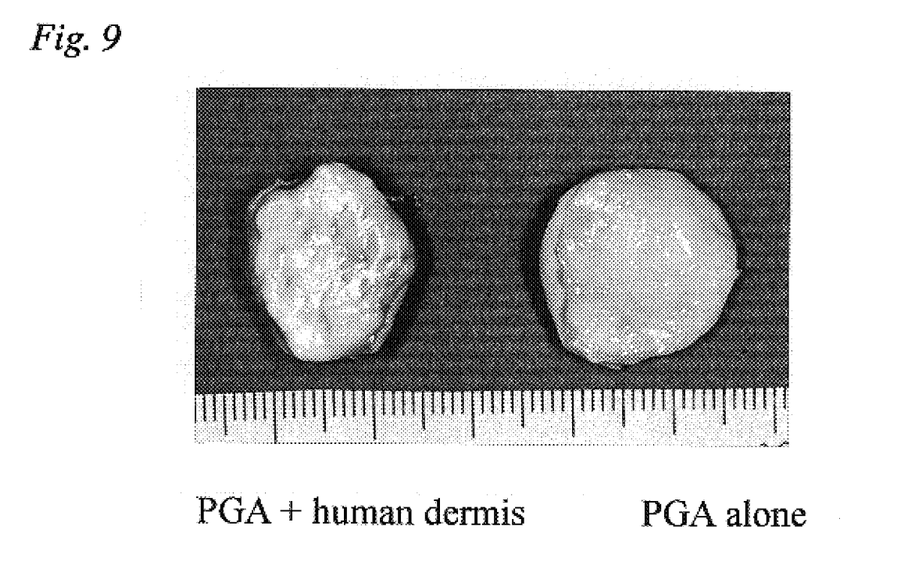
FIG. 9 is a photograph of extracted specimens of a group in which a chondrocyte cell mass was integrated in PGA (Group 1) and a group in which it was further wrapped with human dermis (Group 2).
Figure 10:
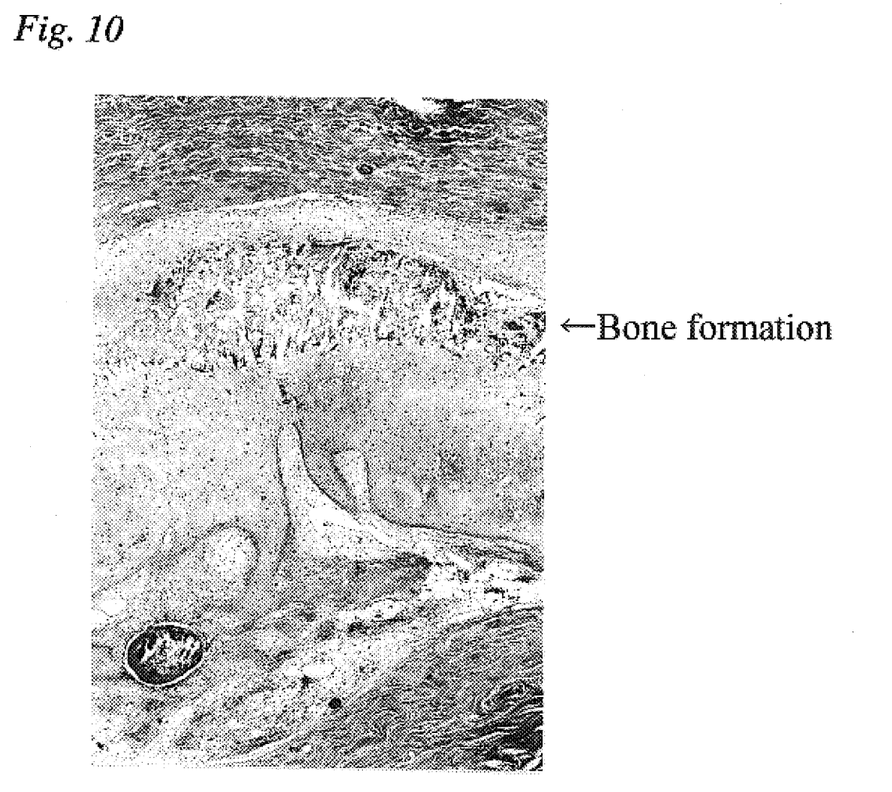
FIG. 10 is a microphotograph showing the tissue of Group 2 in which human dermis was used for wrapping.

(c) The conditions for ossification of the formed cartilage tissue were examined next. (Group 1) A human chondrocyte mass was integrated into PGA and covered with fibrin. (Group 2) Another human chondrocyte mass was integrated into PGA, wrapped with human dermis and then covered with fibrin. Both groups were transplanted under the dorsal skin of nude rats (F344/N rnu/rnu, 6-week-old, 250 g) and formation of cartilage tissue was examined in both groups. Specimens extracted 3 months after the transplant showed Toluidine blue metachromacia specific to cartilage tissue, thus confirming that cartilage tissues had formed in both groups (FIG. 9). In Group 1, in which chondrocyte mass was integrated with PGA alone, only cartilage tissue formation was confirmed. In Group 2, however, in which the mass was wrapped with dermis, vascularization was also observed in the perichondrium and matrix, and cartilaginous ossification was further observed in parts of the cartilage (FIG. 10).

(d) It was then examined whether the cartilage tissue formed after the transplant expressed the characteristics of its origin (the cartilage tissue used for cultivation). Preparations of the above-mentioned specimens were stained with HE (hematoxylin-eosine) staining, Toluidine Blue staining, Alcian blue+PAS staining and EVG (Elastica von Gieson) staining. The cell membrane and interstitium are stained by HE staining, thus allowing observation of cell morphology and confirmation of cartilage tissue formation from the cartilage cavity. The metachromatism observed by Toluidine Blue is specific to cartilage. Alcian blue+PAS staining dyes polysaccharides, thus allowing confirmation of a high amount of cartilage matrix, and especially elastin (glyoprotein) of elastic cartilage. EVG staining dyes elastic fiber, thus allowing confirmation of elastic cartilage (auricular cartilage) formation.

In the case of the cartilage tissue formed from the cultured auricular chondrocytes transplant, the elastic fiber was strongly stained by the EVG staining, and PAS staining was positive in alcian blue+PAS staining, thus identifying them as auricular cartilage cells. In the case of the tissue formed from the cultured costal cartilage transplant, the elastic fiber was weakly stained by EVG staining, while PAS staining was positive in alcian blue+PAS staining, thereby identifying them as costal cartilage cells.

Figure 11:
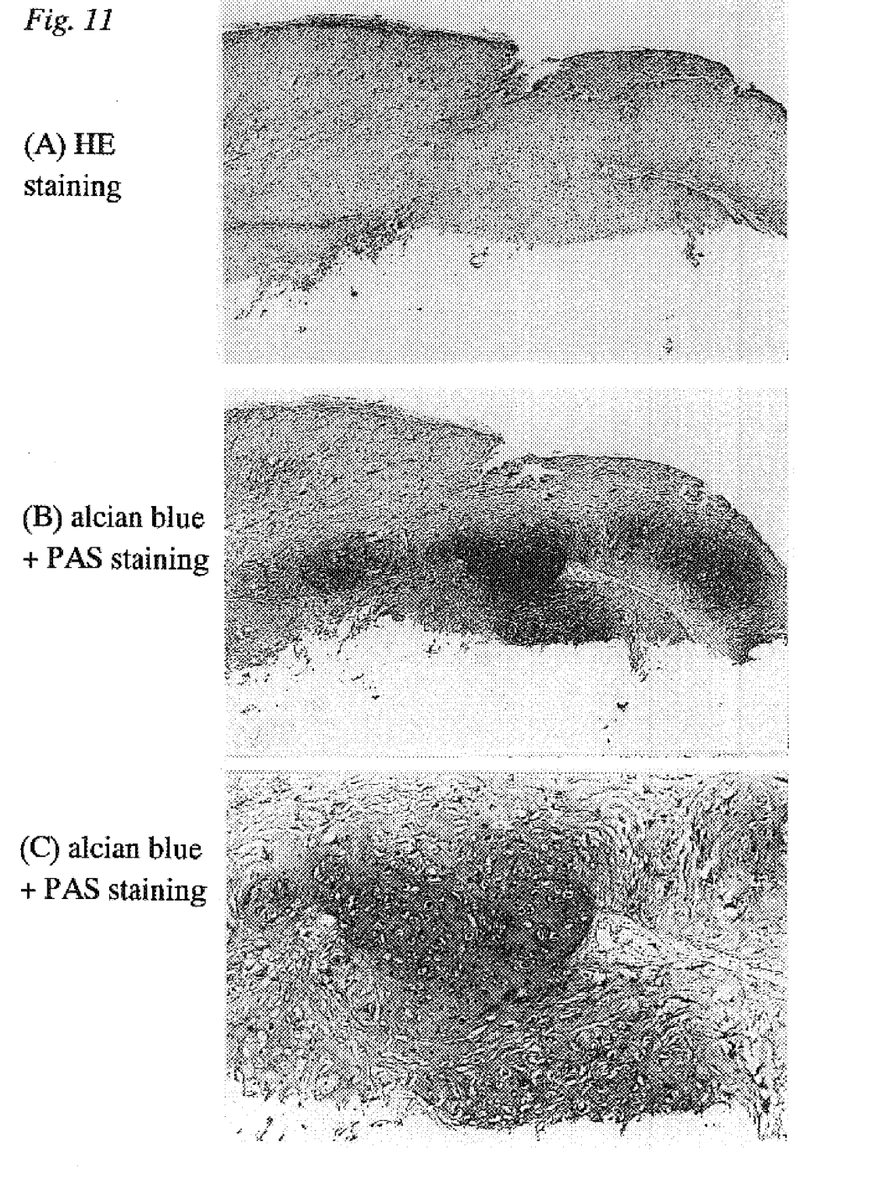
FIG. 11 is a set of microphotographs of (A) HE staining and (B, C) alcianblue+PAS staining of auricular cartilage tissue transplanted with collagen sponge as a support in which chondrocyte mass was integrated.

(e) When a similar transplant experiment was carried out using collagen sponge instead of PGA as support, formation of cartilage tissue was observed in 100 percent of the samples of auricular cartilage (5/5). The transplant specimens were made into preparations and stained with HE staining or alcian blue+PAS staining, and it was confirmed that cartilage tissue had formed (positive in HE staining) and that the formed cartilage tissue was auricular cartilage (positive in alcian blue+PAS staining) (FIG. 11). Formation of cartilage tissue was also confirmed when the same experiment was repeated with costal cortilage.

Figure 12:
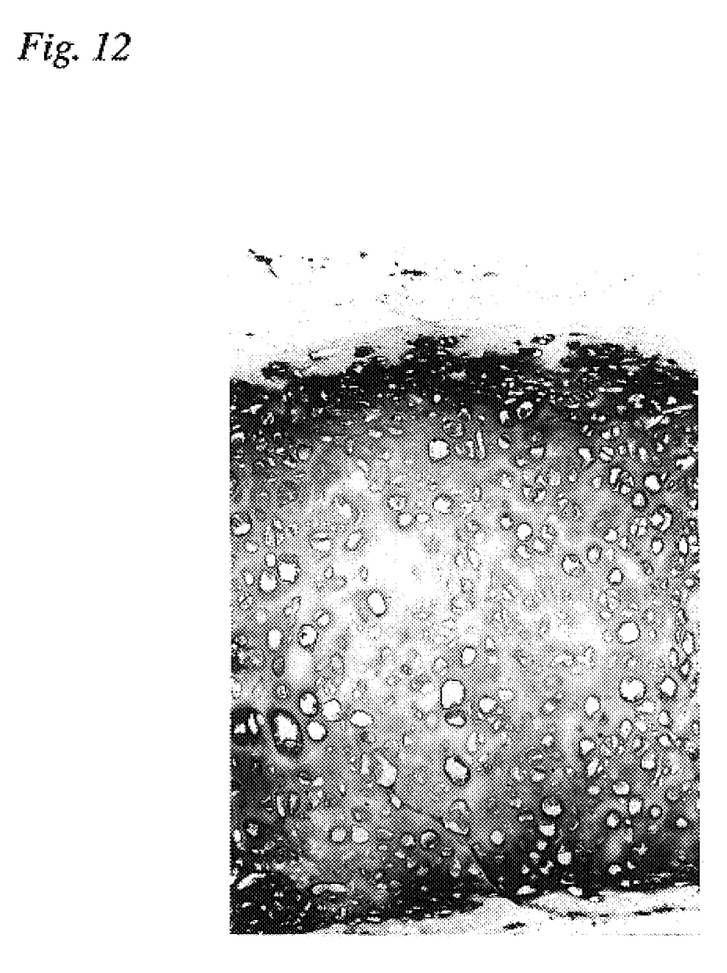
FIG. 12 is a microphotograph of immunological staining of transplanted auricular cartilage tissue using anti-type II collagen.

(f) To confirm that the tissues after the transplant were human derived, antibody staining was carried out by the ABC-PC (peroxidase) method using anti-human type II collagen antibody. As a result, expression of human type II collagen was observed in both auricular cartilage and costal cartilage, thus confirming that the tissues were of human origin (FIG. 12). The results are shown in the following table.

TABLE 2

|  | Auricular cartilage | Costal cartilage |
| --- | --- | --- |
| HE staining | + | + |
| Toluidine Blue metachromatism | + | + |
| PAS staining | ++ | + |
| EVG staining | ++ | +/− |
| Human type II collagen | + | + |

(g) To further confirm that the formed cartilage tissue was of human origin, RT-PCR was performed with type II collagen. RT-PCR was carried out using the following primers having nucleotide sequences specific to human or mouse type II collagen, and the PCR products were treated with the restriction enzyme EcoRI.

```
Human;
Forward primer:
5'-ACATACCGGTAAGTGGGGCAAGAC-3'    (SEQ ID NO: 1)

Reverse primer:
5'-AGGTCTTACAGGAAGACAATAAAT-3'    (SEQ ID NO: 2)

Mouse;
Forward primer:
5'-ATTTTGCAGTCTGCCCAGTTCAGG-3'    (SEQ ID NO: 3)
and

Reverse primer:
5'-AGGTCTTACAGGAAGACAATAAAT-3'    (SEQ ID NO 4)
```

Since human-derived type II collagen is cleaved by EcoRI, it can be easily identified whether it is of human origin or mouse origin. RT-PCR was performed using samples 3 months after transplant from mice transplanted with cultured human chondrocytes tissue, with feeder cells alone and with feeder cells+cultivated human chondrocytes, and, as a control sample, mouse cells. A conventional protocol was used for extracting the RNA from the samples and for the RT-PCR, according to "Gene Manipulation Manual" printed by Igaku-Shoin (published in 1995).

Figure 13:
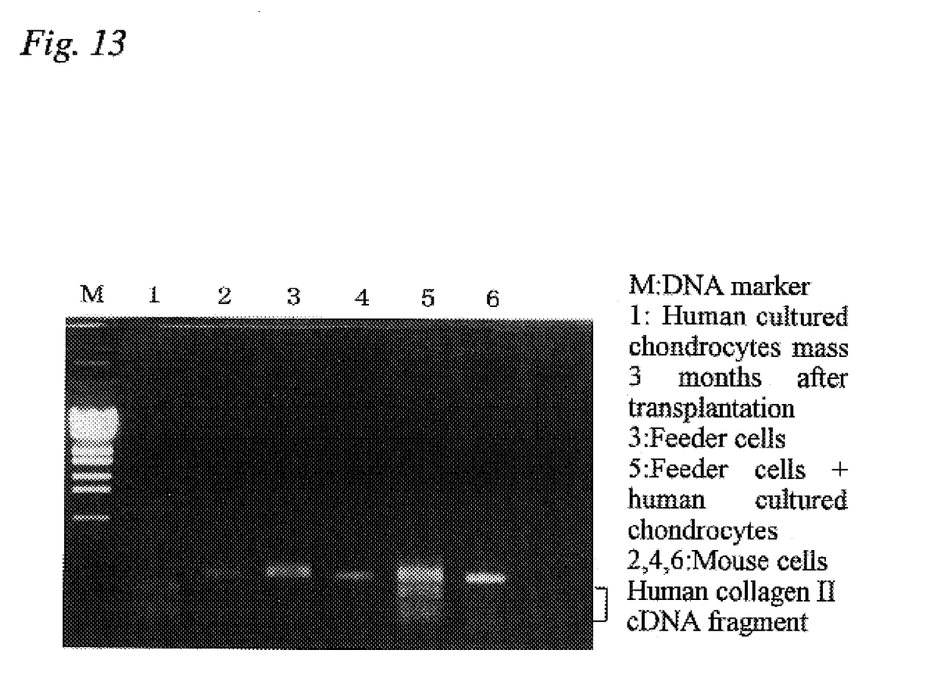
FIG. 13 is a photograph showing the result of RT-PCR for type II collagen of transplanted cartilage tissue.

With the sample transplanted of cultured human chondrocyte tissue, two bands were observed, indicating only human type II collagen. With the samples transplanted with feeder cells alone, digestion by EcoRI did not occur, indicating only mouse type II collagen. With the sample transplanted with the feeder cells+cultivated human chondrocytes, a band for cleavage by the restriction enzyme and a band for no cleavage were observed, indicating both mouse and human type II collagen. With mouse cells as the control, digestion by EcoRI did not occur, indicating only mouse type II collagen. These results confirmed that the cartilage tissue formed after transplant was of human origin. The results are shown in FIG. 13.

INDUSTRIAL APPLICABILITY

The present invention enables rapid culturing of large amounts of human chondrocytes by co-culturing human chondrocytes with perichondral cells in the chondrogenic stage, which are employed as feeder cells to support the proliferation ability of the chondrocytes. A human chondrocyte mass can be obtained by multilayer seeding and culturing of the obtained human chondrocytes one or more times. Cartilage therapy materials in which human chondrocytes or their cell mass is integrated can be produced. Appropriate selection of the material in which the chondrocytes are integrated allows the cartilage therapy material to induce not only generation of cartilage tissue, but also cartilaginous ossification. They are therefore useful for the treatment of diseases involving cartilage and bone.

The invention claimed is:

1. A method for culturing human chondrocytes, comprising co-culturing human chondrocytes with feeder cells, thereby increasing the proliferation of said chondrocytes, and wherein said feeder cells are perichondral cells in the chondrogenic stage and the proliferation ability of said feeder cells is eliminated before co-culturing.

2. The method of claim 1, wherein the perichondral cells are isolated from a mammalian fetus.

3. The method of claim 2, wherein the perichondral cells are derived from first arch cartilage tissue.

4. The method of claim 2, wherein the perichondral cells are isolated from a 13-day-old mouse live fetus.

5. The method of claim 3, wherein the perichondral cells are Meckel perichondral cells.

6. The method of claim 1, wherein the perichondral cells are treated by radiation or chemical treatment before co-culturing, thereby eliminating the proliferation ability of said perichondral cells.

7. The method of claim 6, wherein the perichondral cells are treated by cobalt radiation before co-culturing, thereby eliminating the proliferation ability of said perichondral cells.

8. A method for producing a gel-like chondrocyte mass, comprising co-culturing human chondrocytes with feeder cells, thereby increasing the proliferation of said chondrocytes, and wherein said feeder cells are perichondral cells in the chondrogenic stage and the proliferation ability of said feeder cells is eliminated before co-culturing, then seeding thus-cultured human chondrocytes in at least one multilayer and culturing the seeded human chondrocytes.

9. Feeder cells for culturing human chondrocytes, wherein said feeder cells are perichondral cells in the chondrogenic stage which are derived from first arch cartilage cells isolated from a 13-day-old mouse live fetus and the proliferation ability of said feeder cells is eliminated before co-culturing.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
acataccggt aagtggggca agac                                              24

<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
aggtcttaca ggaagacaat aaat                                              24

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
attttgcagt ctgcccagtt cagg                                              24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
aggtcttaca ggaagacaat aaat                                              24
```